United States Patent [19]

Jacques et al.

[11] Patent Number: 4,504,595

[45] Date of Patent: Mar. 12, 1985

[54] FLUORINATED SILICA CATALYST AND PREPARATION OF AROMATIC/ALIPHATIC NITRILES IN THE PRESENCE THEREOF

[75] Inventors: Roland Jacques, Ales; Michel Reppelin, Collonges-au-Mont-d'Or; Laurent Seigneurin, Salindres, all of France

[73] Assignee: Rhone-Poulenc Specialites Chimiques, Courbevoie, France

[21] Appl. No.: 378,192

[22] Filed: May 14, 1982

[30] Foreign Application Priority Data

May 15, 1981 [FR] France .................... 81 09693

[51] Int. Cl.$^3$ .................. B01J 27/10; B01J 21/08; C01B 33/12; C07C 120/10
[52] U.S. Cl. .................... 502/224; 252/315.6; 260/465 B; 423/338; 502/233
[58] Field of Search ............... 502/224, 233; 423/338, 423/339; 252/315.6

[56] References Cited

U.S. PATENT DOCUMENTS

| | | | |
|---|---|---|---|
| 2,386,810 | 10/1945 | Marisic et al. | 423/338 |
| 2,483,868 | 10/1949 | Archer et al. | 252/315.6 |
| 2,516,967 | 8/1950 | Elam | 252/315.6 |
| 2,794,002 | 5/1957 | Haensel et al. | 502/330 |
| 3,494,875 | 2/1970 | Le Page et al. | 423/338 |
| 4,436,669 | 3/1984 | Jacques et al. | 502/224 |
| 4,438,042 | 3/1984 | Jacques et al. | 502/224 |

*Primary Examiner*—P. E. Konopka
*Attorney, Agent, or Firm*—Burns, Doane, Swecker & Mathis

[57] ABSTRACT

An improved fluorinated siliceous catalyst, well adapted for the catalytic synthesis of aromatic/aliphatic nitriles from their corresponding formamides, formanilides or amides, is comprised of a plurality of silica particulates, the specific surface of which ranging from about 200 to about 300 m$^2$/g, having a total pore volume ranging from about 1 to about 1.5 cm$^3$/g, with an average pore diameter ranging from about 100 to about 200 Å, having an exchange pH of less than about 3, and with the fluorine content thereof bonded to the silica, expressed in F$^-$, ranging from about 0.05 to about 2% by weight based upon the silica, and the sodium content thereof, expressed as Na$_2$O, being less than about 1% by weight, also based upon the silica.

10 Claims, No Drawings

FLUORINATED SILICA CATALYST AND PREPARATION OF AROMATIC/ALIPHATIC NITRILES IN THE PRESENCE THEREOF

BACKGROUND OF THE INVENTION

1. Field of the Invention

The present invention relates to certain novel silica catalysts comprising fluorine values, to a process for the preparation of such silica catalysts, and to the use thereof in the preparation of aromatic or aliphatic nitriles from corresponding formanilides, formamides or amides.

2. Description of the Prior Art

It is known to this art, from French Pat. No. 952,192, to prepare a silica containing fluorine and sodium values from sodium silicate. According to the particular process described therein, dissolved sodium silicate is added to a solution of excess sulfuric acid, and thereafter potassium fluoride is introduced thereto. Stated differently, over the course of the process, the formation of the silica is initially assisted by the reaction of sulfuric acid with sodium silicate, then the excess sulfuric acid reacts with the potassium fluoride subsequently introduced to yield hydrofluoric acid, which acid then impregnates the silica sol formed. In this manner, a silica is obtained which contains fluorine (the fluorine is essentially in the form of potassium fluorosilicate) and the specific surface of which is never less than 450 $m^2/g$, but often greater than 600 $m^2/g$, with a pore volume of about 80 $cm^3/100$ g, and with the average diameter of the pores ranging from about 60 to about 90 Å.

And per the aforecited patent, the product silica is useful as catalyst for such processes as cracking, reforming, isomerization, polymerization and alkylation.

SUMMARY OF THE INVENTION

Accordingly, a major object of the present invention is the provision of an improved fluorinated silica, containing but a minor amount of sodium, and which novel silica is well adapted as catalyst for the preparation of aromatic/aliphatic nitriles, a field of use conspicuously divorced from those suggested in the aforesaid '192 French patent.

Briefly, the present invention features a fluorinated silica, the specific surface of which ranging from about 200 to about 300 $m^2/g$, having a total pore volume ranging from about 1 to about 1.5 $cm^3/g$, with the average diameter of the pores ranging from about 100 to about 200 Å, with an exchange pH of less than about 3, and with the fluorine content thereof bonded to the silica, expressed in $F^-$, ranging from about 0.05 to about 2% by weight based upon the silica, and the sodium content expressed in $Na_2O$ being less than about 1% by weight, also based upon the silica.

The exchange pH is defined herein as that pH measured from a solution of 10 g silica in 100 g pure $H_2O$ at 20° C.

By "fluorine bonded to silica" as utilized herein, there is intended fluorine which is not combined in the known fluosilicate or fluoride form.

DETAILED DESCRIPTION OF THE INVENTION

More particularly according to this invention, in a preferred embodiment thereof, the product fluorinated silica has a specific surface ranging from about 200 to about 250 $m^2/g$, a total pore volume ranging from about 1 to about 1.3 $cm^3/g$, an average pore diameter ranging from about 100 to 150 Å, an exchange pH ranging from about 1 to 3, and having a fluorine content ranging from about 0.1 to 1% and a sodium content of less than about 0.15%.

Thus, the fluorinated silica prepared consistent herewith differs from that of the prior art in that same is characterized as microporous acid silica, containing fluorine directly bonded to the silica.

This invention also features a process for the preparation of the aforesaid novel silica. The basic principal of such improved process, and which is indeed alien to the state of this art, is the formation of the product silica by reaction between the sodium silicate and hydrofluoric acid.

In capsule summary, the process according hereto for the preparation of fluorinated silica containing sodium, comprises adding an aqueous solution of sodium silicate to an aqueous solution of hydrofluoric acid, at a temperature ranging from about $-5°$ C. to about 15° C., while maintaining in the reaction medium a content in $SiO_2$ of less than about 15% by weight of said reaction medium until the pH thereof attains a value ranging from about 3 to about 4.5; next permitting the mixture to gel, and comminuting the resultant hydrogel into grains, with such grains then being washed to eliminate soluble fluoride and lastly dried at a temperature ranging from about 150° to 600° C.

The lower the temperature of reaction between the sodium silicate and the hydrofluoric acid, the greater the proportion of $SiO_2$ may be.

The lower the pH upon termination of the reaction, the longer will be the time required for final gelling.

According to a preferred embodiment of the invention, a sodium silicate is employed containing $SiO_2$ and $Na_2O$ in a molar ratio equal to about 3.

In another preferred embodiment of the invention, from about 1 to about 1.5 mole of HF per mole of $SiO_2$ is used.

Preferably, a temperature ranging from about 0° to 10° C. is maintained during the mixing of the solutions of sodium silicate and hydrofluoric acid, with the $SiO_2$ content being maintained at a value less than about 10%.

The addition of the hydrofluoric acid is preferably discontinued when the pH attains a value ranging from about 3.8 to about 4.5.

To carry out the process of the invention, a highly concentrated solution of hydrofluoric acid and a highly dilute solution of sodium silicate, or, conversely, a highly dilute solution of hydrofluoric acid and a highly concentrated solution of sodium silicate, are advantageously used. For practical purposes, it is preferred to use both solutions having a medium concentration, for example, of about 40 to 50% by weight.

Also advantageously, the hydrogel is comminuted such as to provide grain particles having an average diameter of 2 to 6 mm.

Washing is effected by any means known to those skilled in the art. In a preferred embodiment of the invention, wash water having a pH ranging from about 7 to about 10 is used, and the washing is continued to complete elimination of any soluble salts, as is also well known to those skilled in this art.

Final drying is preferably carried out at a temperature ranging from about 150° C. to about 300° C., for approximately 10 to 24 hours.

In practice, but not as a critical parameter hereof, a carboxylic acid soluble in an aqueous medium, such as acetic acid, is employed simultaneously with the hydrofluoric acid, which leads to an improved control of the variation in pH. Preferably, an amount of the carboxylic acid is used such that the molar ratio of the carboxylic acid to the hydrofluoric acid ranges from about 0.05 to about 0.15.

Another object of this invention is the preparation of aromatic or aliphatic nitriles having the formula:

$$Ar-A-CN \qquad (I)$$

wherein Ar represents a substituted or unsubstituted benzene radical and A represents a direct chemical bond or a hydrocarbon radical having from 1 to 6 carbon atoms, by heating to a temperature ranging from about 450° C. to about 550° C. a formamide or a formanilide having the formula:

$$Ar-A-NHCHO \qquad (II)$$

or an amide having the formula:

$$Ar-A-CONH_2 \qquad (III)$$

wherein Ar and A are as above defined, in the presence of that novel silica catalyst prepared as above outlined.

By "benzene radical (Ar)" as utilized herein, there is intended a phenyl radical or a phenyl radical containing one or more substituents. Exemplary of such substituents are alkyl and alkoxy radicals having from 1 to 6 carbon atoms, phenyl and phenoxy radicals, and the radicals F, CF$_3$, OCF$_3$, SCF$_3$, OH, Cl, Br or CN.

Thus, according to one process of this invention, the following compounds having the Formula I are conveniently prepared: benzonitrile, 3-trifluoromethylbenzonitrile, 4-trifluoromethylbenzonitrile, 4-methoxybenzonitrile, 4-hydroxybenzonitrile, 2-fluorobenzonitrile, 3-fluorobenzonitrile, 4-fluorobenzonitrile, 2-chlorobenzonitrile, 3-chlorobenzonitrile, 4-chlorobenzonitrile, 2-chloro-5-trifluoromethylbenzonitrile, 3-trifluoromethyl-4-chlorobenzonitrile, 3-phenoxybenzonitrile, 3,5-bis-trifluoromethylbenzonitrile, 2,6-dichlorobenzonitrile, 2,6-difluorobenzonitrile, 2,4-difluorobenzonitrile, 3-trifluoromethylthiobenzonitrile, 3-trifluoromethylphenylacetonitrile, 4-trifluoromethylphenylacetonitrile, 4-fluorophenylacetonitrile, 4-chlorophenylacetonitrile, 2-fluorophenylacetonitrile, 2-chlorophenylacetonitrile, 2-trifluoromethoxyphenylacetonitrile, 4-trifluoromethoxyphenylacetonitrile, 2-trifluoromethylthiophenylacetonitrile, 4-trifluoromethylthiophenylacetonitrile, 2-fluoro-5-methylphenylacetonitrile, 3-fluoro-6-methylphenylacetonitrile, 2-chloro-5-trifluoromethoxyphenylacetonitrile, 2-trifluoromethoxy-5-chlorophenylacetonitrile, 2,5-difluorophenylacetonitrile, 2,4-difluorophenylacetonitrile.

The following compounds are representative of those of Formula II suitable as starting materials in the process of the invention: formanilide, 3-trifluoromethylformanilide, 4-trifluoromethylformanilide, 4-methoxyformanilide, 4-hydroxyformanilide, 2-fluoroformanilide, 3-fluoroformanilide, 4-fluoroformanilide, 2-chloroformanilide, 3-chloroformanilide, 4-chloroformanilide, 2-chloro-5-trifluoromethylformanilide, 3-trifluoromethyl-4-chloroformanilide, 3-phenoxyformanilide, 3,5-bis-trifluoromethylformanilide, 2,6-dichloroformanilide, 2,6-difluoroformanilide, 2,4-difluoroformanilide, 3-trifluoromethylthioformanilide, 4-trifluoromethoxyformanilide, benzylformamide, 3-trifluoromethylbenzylformamide, 4-trifluoromethylbenzylformamide, 4-fluorobenzylformamide, 4-chlorobenzylformamide, 2-fluorobenzylformamide, 2-chlorobenzylformamide, 2-trifluoromethoxybenzylformamide, 4-trifluoromethoxybenzylformamide, 2-trifluoromethoxybenzylformamide, 4-trifluoromethoxybenzylformamide, 2-trifluoromethylthioenzylformamide, 4-trifluoromethylthiobenzylformamide, 2-fluoro-5-methylbenzylformamide, 3-fluoro-6-methylbenzylformamide, 2-chloro-5-trifluoromethoxybenzylformamide, 2-trifluoromethoxy-5-chlorobenzylformamide, 2,5-difluorobenzylformamide, 2,4-difluorobenzylformamide.

And exemplary of the compounds of the Formula III are: 3-trifluoromethylbenzamide, 4-trifluoromethylbenzamide, 2-fluorobenzamide, 3-fluorobenzamide, 4-fluorobenzamide, 3-trifluoromethylphenylacetamide, 4-fluorophenylacetamide, 4-trifluoromethoxyphenylacetamide.

It is known to this art, from French Pat. No. 1,250,165, to prepare nitriles from N-formylamine compounds by reactively contacting the same, at a temperature ranging from 460° to 560° C., and in the gaseous phase, with a catalyst comprising active silicic acid or silicates, at least 75% of the pores of which having a radius ranging from 10 to 200 Å, with an average pore radius ranging from 20 to 100 Å and having a specific surface of at least 550 m$^2$/g, and also containing a metal oxide, such as titanium dioxide.

Nonetheless, carrying out the subject reaction with catalysts of the type described in the aforecited French patent evidences that, when the starting material is an N-formylamine bearing a fluorine substituent, the process promotes the formation of heavy by-products which shortens the life of the catalyst by encrusting its surface, and defluorination reactions too are observed, resulting in compounds which are extremely difficult to separate from the desired product.

Thus, it has now surprisingly been found that the use of the novel fluorinated silica catalyst in a nitrile synthesis consistent herewith enables the very appreciable reduction of formation of objectionable heavy by-products and the virtual elimination of competing defluorination reactions. The immediately aforesaid is of heightened interest on an industrial scale, because the nitriles prepared according to this embodiment of the invention are very important intermediates for the synthesis of a variety of compounds having phytosanitary or pharmaceutical activity.

Hence, this particular embodiment of the invention is especially well adapted for the catalytic conversion of a starting material having the Formula II or Formula III wherein the phenyl radical of which bears one or more of the fluorine substituents F, CF$_3$, OCF$_3$ or SF$_3$.

Such process embodiment is even more suited to the use of compounds having the Formula II and bearing a fluorine substituent. Among the latter, meta-trifluoromethylformanilide:

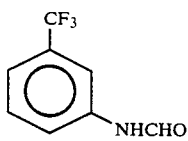

and meta-trifluoromethylbenzylformamide:

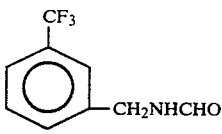

are representative.

In another, but non-critical embodiment of the invention, the reaction is carried out in the presence of a gaseous inert diluent, consisting preferably of nitrogen and/or $CO_2$ and/or acetonitrile.

It is preferred to use acetonitrile in an amount such that the molar percentage of the compound having the Formula II or III in the acetonitrile ranges from about 2 to about 20, and preferably from about 5 to about 10.

The reaction temperature preferably ranges from about 510° to 530° C. when a compound of the Formula II is employed, and from 450° to 480° C. when a compound of the Formula III is employed.

The reaction is typically conducted at atmospheric pressure, albeit pressures greater or less than atmospheric too are within the ambit of the invention.

The process according to the invention is advantageously carried out at a space velocity of from about 0.2 to about 4 moles of the compound II or III per hour and per liter of the catalyst.

The compounds III are per se known to the art and may be prepared by any known method.

Likewise, the preparation of the compounds II, when A is a direct chemical bond, is carried out in a manner well known to this prior art, by the reaction of the corresponding aniline with formic acid.

In the event that A is a hydrocarbon radical such as —$CH_2$—, the compounds II may conveniently be prepared by the reaction, at 0° to 100° C. and in the presence of hydrofluoric acid, of the corresponding benzene derivative ArH with hydroxymethylformamide, HO—$CH_2$—NHCHO. The ratio of ArH to HO—$CH_2$—NHCHO ranges from about 0.5 to about 2, and that of the hydrofluoric acid to ArH ranges from about 5 to about 50. Such a preparation is featured in Desbois et al copending application, Ser. No. 178,225 filed concurrently herewith and assigned to the assignee hereof.

In order to further illustrate the present invention and the advantages thereof, the following specific examples are given, it being understood that same are intended only as illustrative and in nowise limitative.

EXAMPLE 1

An aqueous solution containing 250 g of 40% HF, 34.7 g of 99% acetic acid and 712 g of water was first prepared. A second aqueous solution of sodium silicate, having a density of 1.185 ($SiO_2/Na_2O=3.3$), was also prepared. The two solutions were next cooled to 5° C. The silicate solution was then poured into the hydrofluoric acid solution which was under vigorous agitation, while maintaining the temperature at 5° C., until the pH reached a value of 4. Next, 2,133 g of the sodium silicate solution were poured therein. The sol which resulted gelled in 10 min. The product hydrogel was comminuted to provide grains having an average diameter of 2 to 6 mm. These grains were then washed with water in a column, the pH of which having been adjusted to 8 by addition of ammonia thereto at ambient temperature for 24 hours. The solids obtained were then dried at 200° C. for 24 hours. The characteristics of the final product silica were as follows:

| (i) | Specific surface: | 223 m²/g |
|---|---|---|
| (ii) | Total pore volume: | 1.30 cm³/g |
| (iii) | Average diameter of pores: | 120 Å |
| (iv) | Sodium ($Na_2O$) content: | 0.072% |
| (v) | Fluorine content: | 0.32% |
| (vi) | Exchange pH: | 3 |

EXAMPLE 2

An aqueous solution containing 250 g of 40% HF, 34.7 g of 99% acetic acid and 712 g of $H_2O$ was first prepared. A second aqueous solution of sodium silicate having a density of 1.185 ($SiO_2/Na_2O=3.3$) was next prepared. The two solutions were then cooled to 10° C. The silicate solution was poured into the vigorously agitated hydrofluoric acid solution until the pH reached a value of 4. 1,720 g of the sodium silicate solution were then poured into such solution, while the temperature was maintained at 10° C. The resulting solution was poured onto a plate where it gelled in 10 min. The resulting hydrogel was comminuted into grains having an average diameter of 2 to 6 mm, which were then washed with water having a pH of 8. The solids obtained were dried at 150° C. for 25 hours, rewashed in distilled water for 36 hours, and then dried at 200° C. for 24 hours. The characteristics of the final product silica were as follows:

| (i) | Specific surface: | 211 m²/g |
|---|---|---|
| (ii) | Total pore volume: | 1.03 cm³/g |
| (iii) | Average diameter of pores: | 119 Å |
| (iv) | Sodium content ($Na_2O$): | 0.046% |
| (v) | Fluorine content: | 0.26% |
| (vi) | Exchange pH: | 3 |

EXAMPLE 3

A first aqueous solution containing 500 g of 40% HF and 2479 g of water was prepared, as was a second aqueous solution of sodium silicate having a density of 1.185 ($SiO_2/Na_2O=3.3$).

Both solutions were cooled to 0° C.

The silicate solution was then poured into the vigorously agitated hydrofluoric acid solution, while the temperature was maintained at from −2° to 2° C. until the pH reached a value of 4 (the concentration of the silica in the sol was 10.67%). 2097 g of the sodium silicate solution were next poured into such solution. The sol obtained gelled in 20 min. The resulting hydrogel was comminuted to provide grains having an average diameter of 2 to 6 mm. These grains are dropped into five times their volume of water over one hour, the pH of the water having been adjusted to 8 by the introduction of ammonia thereto.

The solids obtained were then dried at 200° C. for 25 hours.

The resulting silica was next washed with demineralized water and then dried.

The characteristics of the final product silica were as follows:

| (i) | Specific surface: | 233 m²/g |
|---|---|---|
| (ii) | Total pore volume: | 115 cm³/100 g |
| (iii) | Average pore diameter: | 115 Å |
| (iv) | Na₂O content: | 1200 ppm |
| (v) | Fluorine content: | 0.16% |
| (vi) | Exchange pH: | 3 |

EXAMPLE 4

A first aqeuous solution containing 500 g of 40% HF and 5000 cm³ of H₂O was prepared, as was a second aqueous solution of sodium silicate having a density of 1.185 (SiO₂/Na₂O=3.3).

Both solutions were cooled to 10° C.

The silicate solution was then poured into the vigorously agitated hydrofluoric acid solution until a pH of 4 was reached.

2370 g of the sodium silicate solution were next poured into such solution, while the temperature was maintained at from 8° to 12° C. The concentration of SiO₂ in the sol was 6.77. The resulting solution was poured onto a plate where it gelled in 10 min. The resulting hydrogel was comminuted into grains having an average diameter of 2 to 6 mm. The grains were dropped into five times their volume of water, over 1 hour. The pH of the water had been adjusted to 8 by introduction of ammonia thereto.

The solids obtained were then dried at 200° C. for 24 hours. The dried silica was then washed with demineralized water, and then dried.

The characteristics of the final product silica were as follows:

| (i) | Specific surface: | 195 m²/g |
|---|---|---|
| (ii) | Total pore volume: | 103 cm³/100 g |
| (iii) | Pore diameter: | 120 Å |
| (iv) | Na₂O content: | 1600 ppm |
| (v) | Fluorine content: | 0.31% |
| (vi) | Exchange pH: | 3 |

EXAMPLE 5

Into a stainless steel tubular reactor having a one liter capacity and filled with the catalyst as prepared in Example 2, an optionally preheated admixture of 500 g/h acetonitrile and 125 g/h meta-trifluoromethylformanilide was continuously introduced. The reaction temperature was maintained at 530° C. throughout the catalytic bed. In this manner. a conversion of 95% of the formanilide was realized. Over the course of time, the flow rates were adjusted such as to maintain this rate of conversion. Thus, over 450 hours, 37.20 kg of meta-trifluoromethylformanilide were introduced. The following products were recovered after distillation of the reaction solvent and the water of reaction:
(1) 25.0 kg Meta-trifluoromethylbenzonitrile;
(2) 5.68 kg Meta-trifluoromethylaniline;
(3) 2.39 kg Unconverted formanilide; and
(4) 0.52 kg Heavy products.

The selectivity of the nitrile formed with respect to the formanilide reacted was 98.1%.

In this and the following examples, selectivity is defined as the ratio of product nitrile to the formanilide reacted, excluding the formanilide converted into the corresponding aniline, because the latter, in an industrial process, may be quantitatively converted by means of formic acid into the beginning formanilide and recycled. The fluoride content in the crude mixture exiting the reactor was 130 ppm. The meta-trifluoromethylbenzene contained but trace amounts of benzonitrile and only 0.32% meta-tolunitrile.

EXAMPLE 6

The procedure of Example 5 was repeated, but utilizing the silica prepared in Example 1, and 44.46 kg meta-trifluoromethylformanilide were introduced over the course of 380 hours. After distillation of the solvent and the water of reaction, the following products were recovered:
(1) 28.81 kg Meta-trifluoromethylbenzonitrile;
(2) 9.8 kg Meta-trifluoromethylaniline;
(3) 2.05 kg Meta-trifluoromethylformanilide, unconverted; and
(4) 1.26 kg Heavy products.

The selectivity as regards the nitrile formed was 95.9%. The fluoride content in the crude mixture was 110 ppm. The nitrile obtained after distillation contained but trace amounts of benzonitrile and 0.28% meta-tolunitrile.

COMPARATIVE EXAMPLE 1

The procedure of Example 6 was repeated, but replacing the catalyst with a TiO₂ catalyst according to the process described in Example 1 of French Pat. No. 1,250,165. Over the course of 135 hours, 14.17 kg meta-trifluoromethylformanilide were introduced. The following products were obtained:
(1) 9.93 kg Meta-trifluoromethylbenzonitrile;
(2) 0.85 kg Meta-trifluoromethylaniline;
(3) 0.70 kg Meta-trifluoromethylformanilide, unconverted; and
(4) 1.5 kg Heavy products.

The selectivity as regards the nitrile formed was 88%. The fluoride content in the reaction medium was 1,630 ppm. The nitrile obtained contained 0.35% benzonitrile and 1.45% meta-tolunitrile. After 135 hours, the catalyst was deactivated.

EXAMPLE 7

The procedure of Example 5 was repeated, but with the temperature of the catalytic zone being established at 510° C. and by supplying to the reactor 600 g/h acetonitrile and 150 g/h para-fluoroformanilide. Over the course of 500 hours, 75 g para-fluoroformanilide were introduced and the following products were recovered after distillation of the reaction solvent:
(1) 55 kg Para-fluorobenzonitrile;
(2) 7.1 kg Para-fluoroaniline;
(3) 0.75 kg Para-fluoroformanilide, unconverted; and
(4) 3.02 kg Heavy Products.

The selectivity as regards the nitrile was 96.7%. The fluoride content in the reaction medium was less than 50 ppm. After 500 hours, the catalyst was still active.

EXAMPLE 8

The procedure of Example 5 was repeated, but with the temperature of the catalytic zone being established at 520° C. and by supplying the reactor with 48.36 kg meta-trifluoromethylbenzylformamide and 193.4 kg acetonitrile over the course of 450 hours. Following completion of the reaction, and after the distillation of the reaction solvent and the water of reaction, the following products were recovered:
(1) 38.7 kg Meta-trifluoromethylphenylacetonitrile;
(2) 3.05 kg Meta-trifluoromethylbenzylamine;
(3) 1.5 kg Unconverted meta-trifluoromethylbenzylformamide; and
(4) 0.9 kg Heavy products.

The selectivity as regards the nitrile was 98%. The fluoride content in the overall reaction mixture was 160 ppm. The nitrile obtained after distillation contained less than 0.10% phenylacetonitrile and 0.4% meta-methylphenylacetonitrile.

EXAMPLE 9

In the apparatus described in Example 3 and using the catalyst of Example 2, a mixture of 45 kg para-trifluoromethoxyformanilide and 180 kg acetonitrile was introduced therein over the course of 400 hours. The reaction zone was maintained at 520° C. The following products were obtained:
(1) 35.2 kg Para-trifluoromethoxybenzonitrile;
(2) 2.9 kg Para-trifluoromethoxyaniline;
(3) 1.82 kg Para-trifluoromethoxyformanilide, unconverted; and
(4) 1.26 kg Heavy products.

The selectivity as regards the nitrile was 96.9%. The fluoride content in the reaction medium was 130 ppm.

EXAMPLE 10

The procedure of Example 5 was repeated, but replacing a portion of the acetonitrile with gaseous carbon dioxide, i.e., introducing into the catalyst bed over the first 100 hours of reaction, 350 g/h acetonitrile, 125 g/h meta-trifluoromethylformanilide and 72 l/h TPN of carbon dioxide gas. Thus, over 450 hours, the same amount of formanilide was introduced as in Example 2. The results obtained were identical to those of Example 3.

EXAMPLE 11

The procedure of Example 6 was repeated, utilizing the catalyst obtained according to Example 3, with a temperature of the catalyst bed of 450° C. and by introducing a mixture of 125 g/h meta-trifluoromethylbenzamide and 500 g/h acetonitrile. The conversion was total. At the outlet of the reactor, after condensation, a mixture of meta-trifluoromethylbenzonitrile, acetonitrile and water was collected, together with trace amounts of heavy products. The fluoride content in the reaction mixture was less than 50 ppm. Selectivity as regards the trifluoromethylbenzonitrile was higher than 99%. After 500 hours, the catalyst was still active.

EXAMPLE 12

The procedure of Example 5 was repeated, utilizing the catalyst obtained according to Example 4, and a mixture of 31 kg para-methoxyformanilide and 144 kg acetonitrile was continuously introduced. After an operation of 400 hours, the following products were collected at the reactor outlet:
(1) 22.6 kg Para-methoxybenzonitrile;
(2) 2.61 kg Para-methoxyaniline;
(3) 1.24 kg Unconverted formanilide; and
(4) 0.88 kg Heavy products.

Selectivity as regards the nitrile was 96.7%. After 400 hours, the catalyst was still active.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of the fluorinated siliceous catalyst comprising (i) adding an aqueous solution of sodium silicate to an aqueous solution of hydrofluoric acid, the temperatures of said solutions ranging from about $-5°$ C. to about 15° C.; (ii) maintaining an amount of $SiO_2$ in the resulting reaction medium of less than about 15% by weight thereof, until the pH of said reaction medium attains a value of from about 3 to about 4.5; (iii) next permitting the mixture of reaction to gel, and comminuting the hydrogel which results into grain particles; then (iv) washing said grain particles to eliminate the soluble fluoride values therefrom; and (v) drying said washed grain particles at a temperature ranging from about 150° C. to 600° C.; said catalyst having a specific surface ranging from about 200 to about 300 m$^2$/g, having a total pore volume ranging from about 1 to about 1.5 cm$^3$/g, with an average pore diameter ranging from about 100 to about 200 Å, having an exchange pH of less than about 3 and with the fluorine content thereof bonded to the silica, expressed in $F^-$, ranging from about 0.05 to about 2% by weight based upon the silica, and the sodium content thereof, expressed as $Na_2O$, being less than about 1% by weight also based upon the silica.

2. The process as defined by claim 1, the sodium silicate comprising $SiO_2$ and $Na_2O$ in a molar ratio of about 3.

3. The process as defined by claim 1, comprising employing from about 1 to about 1.5 mole of HF per mole of $SiO_2$.

4. The process as defined by claim 1, said grain particles having an average diameter of from 2 to 6 mm.

5. The process as defined by claim 1, said washing (iv) being with water, the pH of which ranging from about 7 to 10.

6. The process as defined by claim 5, the amount of $SiO_2$ in the reaction medium being maintained at less than about 10% by weight thereof.

7. The process as defined by claim 5, the concentrations of said silicate and HF solutions both ranging from about 40 to 50% by weight.

8. The process as defined by claim 1, wherein a reaction medium soluble organic carboxylic acid is added simultaneously with the hydrofluoric acid.

9. The process as defined by claim 8, wherein the molar ratio of the carboxylic acid added to the hydrofluoric acid ranges from about 0.05 to about 0.15.

10. The process as defined by claim 9, said carboxylic acid being acetic acid.

* * * * *